United States Patent [19]

Partain, III et al.

[11] Patent Number: 4,997,643

[45] Date of Patent: Mar. 5, 1991

[54] POLYMERIC SALT DELIVERY SYSTEMS

[75] Inventors: Emmett M. Partain, III, Bound Brook; George L. Brode, II, Bridgewater, both of N.J.

[73] Assignee: Union Carbide Chemicals and Plastics Company Inc., Danbury, Conn.

[21] Appl. No.: 378,839

[22] Filed: Jul. 12, 1989

[51] Int. Cl.$^5$ .............................................. A61K 31/74
[52] U.S. Cl. ...................................... 424/78; 424/486;
424/45; 424/435; 424/436; 424/443; 424/484
[58] Field of Search ................... 424/443, 45, 78, 435,
424/436, 490, 484, 443

[56] References Cited

U.S. PATENT DOCUMENTS 4,013,820  3/1977  Farhadieh et al. ................. 424/494

Primary Examiner—Merrell C. Cashion, Jr.
Assistant Examiner—Leon R. Horne
Attorney, Agent, or Firm—Paul W. Leuzzi, II

[57]  ABSTRACT

A biocompatible, film-forming delivery system for the delivery of pharmaceutical or therapeutic actives to a desired topical site of a subject, the system including:
an active salt compound, wherein the active salt compound is at least a partial salt of
(1) a carboxylic acid moiety-containing, biocompatible, film-forming polymer with
(2) at least one active selected from the group consisting of pharmaceutical actives, therapeutic actives and a combination thereof, wherein the at least one active is capable of complexing with at least one carboxylic acid moiety of the polymer to form the active salt compound, and
wherein the active salt compound forms an active salt compound film on the topical site and the active salt compound disassociates into the polymer and the at least one active while the delivery system is in contact with the topical site such that the polymer remains thereon as a polymer film and the at least one active is delivered to the topical site in an absorbable form.

19 Claims, No Drawings

POLYMERIC SALT DELIVERY SYSTEMS

FIELD OF THE INVENTION

This invention relates, in general, to novel delivery systems useful for the topical delivery of pharmaceutical or therapeutic actives. In one aspect, this invention relates to delivery systems containing certain salts of a carboxylic acid moiety-containing, biocompatible polymer and such actives which are effective systems for the delivery of a variety of such pharmaceutical and therapeutic actives. In a further aspect, this invention is directed to the preparation and use of such systems.

BACKGROUND OF THE INVENTION

Traditionally, pharmaceutical and therapeutic actives can be administered to the body by a number of routes, including ingestion, injection, inhalation, and topical application. Absorption of an active by ingestion, injection, or inhalation generally gives systemic distribution of the active throughout the body. Systemic distribution of the active may be unsatisfactory for three reasons. First, these modes of administration produce non-specific distribution. The active is distributed through the entire body and not localized. Second, there may be undesirable effects such as toxic or irritating reactions on non-target organs or regions. Finally, to achieve the desired effect at the target organ or region, a higher dosage than might otherwise be desired must be administered to compensate for systemic dilution of the active.

In contrast to systemic delivery, topical delivery is application of an active in a manner so that it acts primarily at the site of application. The above-described deficiencies of systemic delivery are not encountered when an active is applied topically. Rather, topical application affords the opportunity to minimize the dosage and confine the active to the region of the body to which it is applied. Thus, systemic distribution of the active throughout the body is obviated. Typical sites of topical delivery include application to the dermal, ophthalmic, and mucous membranes and tissues, such as the hair, skin, eyes, ears, mouth, nose, throat, rectum, vagina, and urethra.

However, despite these advantages of topical delivery, most current topical delivery formulations are inefficient and therefore have limited utility. There are three reasons for this inefficiency of current topical delivery technology. First, skin and mucous membranes possess good barrier properties and the permeability of most actives through these barriers generally is poor. Second, actives applied topically are subject to migration and loss due to perspiration, natural tissue lavation, and mechanical action particularly because such actives are not substantive, not readily absorbed by the skin, and do not form films. Third, because most pharmaceutical or therapeutic actives are relatively simple, low molecular weight compounds or mixtures, these actives have limited solubility in common solvents such as water and alcohol. The actives tend to crystallize and flake-off the skin, for example, before they can be absorbed.

Consequently, considerable effort has been and is being expended in search of a proper delivery system which can minimize undesirable crystallization of the active, deliver the active to the application site, control the dosage thereof, and optimize its availability in its active form. Most known topical delivery systems are petrolatum-based cremes and ointments. These unctuous formulations are unsatisfactory because they are at best uncomfortable and messy when applied to skin and mucous membrane (mucosa).

A topical delivery system cannot be considered fully satisfactory if it is deficient with regard to any of the above-described criteria. For example, a delivery system which does not ensure that the active efficiently penetrates the application site is not satisfactory because it requires that an excess of active be incorporated into the delivery system to ensure delivery of an effective quantity. The remaining active, i.e., that which does not penetrate the application site, is wasted. Similarly, active which is allowed to migrate from the application site, or to crystallize before it penetrates the site, is wasted. Further, a delivery system which satisfies each criterion will be adjudged a failure by a consumer who is dissatisfied because the delivery system leaves an unpleasant residue. For example, an unctuous residue, which is unpleasant to the touch and messy, may cause a consumer not to utilize the treatment. Thus, such delivery systems are unsatisfactory.

SUMMARY OF THE INVENTION

Accordingly, the present invention is directed to novel delivery systems comprised of certain salts of a carboxylic acid moiety-containing, biocompatible polymer and a pharmaceutical or therapeutic active. Optionally, the delivery system may also include a delivery enhancer. The invention also relates a method for preparing the delivery systems, and to a method for their application to a subject.

The delivery system of the present invention is a biocompatible, film-forming delivery system for the delivery of pharmaceutical or therapeutic actives to a desired topical site of a subject. The system comprises:
an active salt compound, wherein the active salt compound is at least a partial salt of
  (1) a carboxylic acid moiety-containing, biocompatible, film-forming polymer with
  (2) at least one active selected from the group consisting of pharmaceutical actives, therapeutic actives and a combination thereof, wherein the at least one active is capable of complexing with at least one carboxylic acid moiety of the polymer to form the active salt compound, and
wherein the active salt compound forms an active salt compound film on the topical site and the active salt compound disassociates into the polymer and the at least one active while the delivery system is in contact with the topical site such that the polymer remains thereon as a polymer film and the at least one active is delivered to the topical site in an absorbable form.

The system efficiently delivers the actives to the user at the application site and provides at the site a non-irritating, essentially imperceptible, gas permeable film over the application site.

DETAILED DESCRIPTION OF THE INVENTION

This invention is based on the discovery that a delivery system for pharmaceutical or therapeutic actives comprising:
an active salt compound, wherein the active salt compound is at least a partial salt of (1) a carboxylic acid moiety-containing, biocompatible, film-forming polymer with
(2) at least one active selected from the group consisting of pharmaceutical actives, therapeutic actives and a combination thereof, wherein the at least one active is capable of complexing with at least one carboxylic acid moiety of the polymer to form the active salt compound, and wherein the active salt compound forms an active salt compound film on the topical site and the active salt compound disassociates into the polymer and the at least one active while the delivery system is in contact with the topical site such that the polymer remains thereon as a polymer film and the at least one active is delivered to the topical site in an absorbable form;

provides unexpectedly efficient delivery of the active.

Optionally, a delivery enhancer may be added to further enhance the efficiency of the delivery of the active to the application site.

As used throughout the specification and claims, the phrase "pharmaceutical active" is considered to be a drug, i.e., a substance which, when applied to or introduced into the body, alters body functions in some way. The phrase "therapeutic active" is broader in scope and includes any substance which is capable of altering either body function or cosmetic appearance, but which is not traditionally or technically considered a drug. For example, mineral oil does alter the skin in at least a cosmetic manner or in some cases may be therapeutic. Therefore, mineral oil is considered to be a "therapeutic active" for purposes of the present invention.

There are several features which make the delivery systems of the present invention superior delivery vehicles. In the first instance, the delivery systems of this invention are preferably substantive with hair, skin, and mucous membrane. Throughout the specification and claims, the term "substantive" means that there exists a cohesive or adhesive interaction between the carboxylic acid moiety-containing, biocompatible polymer and salts thereof and a proteinaceous substrate, i.e., the hair, skin, or mucosa, to which the delivery system is applied. In the delivery systems of the present invention, substantivity typically is obtained by ensuring that the polymer is amphoterically or hydrophobically or cationically modified. Incorporation of appropriate hydrophobic groups, amphoteric groups or cationic groups or combinations there of provide substantivity.

If the polymer does not already contain anhydride moieties thereon, hydrophobic groups may be incorporated into the polymer by first converting a portion of the carboxylic acid moieties thereof into cyclic anhydride moieties. These cyclic anhydride moieties are then derivatized with a primary, secondary or tertiary alcohol or a primary or secondary amine to give the half-ester or half-amine derivatives of the polymer, respectively.

These alcohols and amines preferably have at least eight carbons therein. The alcohols may be alkyl alcohols, alkaryl alcohols and aralkyl alcohols, preferably alkyl alcohols. The amines are preferably alkyl amines. Dodecyl alcohol and dodecyl amine are examples of an alkyl alcohol and an alkyl amine, respectively.

The polymer may be amphoterically modified by reacting the polymer with cationic alcohols, for example, choline chloride, and/or quaternary compounds, for example, hydroxy propyl trimethyl ammonium chloride. Thus, the delivery systems of the present invention may be tailored to exhibit a cohesive interaction with the proteins of hair, skin, and mucosa.

The carboxylic acid moiety-containing, biocompatible polymers and active salts thereof utilized in the delivery system of the present invention are those which are good film-formers, i.e., a polymeric film is readily formed when a solution of these polymers and/or salts in a biocompatible solvent is applied topically. Upon topical application of the delivery system of this invention, a polymeric film forms and the active salt thereof serves as a reservoir from which the active is continuously delivered. The film also serves to protect the application site from insult or injury.

Biocompatible solvents are well-known by those skilled in the art. Water, ethanol, propylene glycol, hexylene glycol, glycerine, and mixtures thereof are the most commonly used biocompatible solvents. Additionally, such biocompatible solvents may be utilized which provide other desirable functions in a delivery system. Such secondary functions of biocompatible solvents are also well-known by those skilled in the art.

The hydrophobically and/or cationically and/or amphoterically derivatized polymers exhibit substantive properties to keratin and other protein constituents of hair, skin, and mucosa. Thus, upon application of these materials to these tissues, the resulting film is bound to the tissue. This close relationship minimizes loss or migration of the film and the active. Any form of the delivery system, such as a gel, a lotion (solution of a non-aqueous fraction and an aqueous fraction), creme or ointment (both emulsions), spray (aerosol or powder, for example) comprising the active salt compound conveniently may be utilized to form the subject delivery system. The system may also be applied to the skin or mucosa in the form of a pre-formed film, sponge, powder or other composite, as described below.

Application of an active salt compound-containing delivery system which forms a film provides uniform distribution of the active on the issue and prevents migration or loss of the active from the site of application. The reservoir of active in the film helps to control the rate of release. The biocompatible polymers and active salts of the present invention are those which do not elicit an inflammatory, allergic, or pyrogenic response in humans. In addition, the films these materials form on skin and mucosa are preferably selected so as to be essentially imperceptible to the patient and cosmetically comfortable to wear. The making of such selections is within the capabilities of one skilled in the art without undue experimentation.

The carboxylic acid moiety-containing, biocompatible, film-forming polymers utilized herein are selected from the class of polycarboxylic acid polymers and from the class of cyclic anhydride moiety-containing polymers. The polymer may be a homopolymer, copolymer or graft polymer. The homopolymer is a polymer of an ethylenically unsaturated mono-carboxylic acid or an ethylenically unsaturated poly-carboxylic acid or cyclic anhydride thereof. The copolymer is a polymer of an ethylenically unsaturated mono-carboxylic acid and/or an ethylenically unsaturated poly-carboxylic acid or cyclic anhydride thereof copolymerized with one or more ethylenically unsaturated non-carboxylic acid-containing monomers. The graft polymer is a homopolymer or copolymer of at least one ethylenically unsaturated, non-carboxylic acid-containing monomer to which is grafted an ethylenically unsaturated mono-carboxylic acid or an ethylenically unsaturated poly-carboxylic acid or cyclic anhydride thereof. The homopolymer and copolymer may be the product of polymerizing one or more conjugated-dienes, such as butadiene or isoprene, which are then selectively hydrogenated leaving a residual amount of ethylenic unsaturation therein at which ethylenically unsaturated carboxylic acids may be grafted. Generally, polymerization and hydrogenation are carried out in solution with a suitable catalyst therefor. The grafting reaction may take place in solution or in the melt, such as in an extruder. Such polymerization, copolymerization and grafting processes and methods are well-known to those skilled in the art, as well as selective hydrogenation.

The ethylenically unsaturated carboxylic acids utilized in the polymers hereof preferably have 2 to about 10 carbon atoms excluding those in the carboxyl and/or cyclic anhydride groups thereof.

Examples of such ethylenically unsaturated monocarboxylic acids include, but are not limited to, acrylic acid, methacrylic acid, crotonic acid, and the like. Oligomers or polymer sequences of these monomers may be capable of forming a cyclic anhydride which may be utilized to incorporate hydrophobic moieties into the polymer or cationically-charged moieties into the polymer.

The ethylenically unsaturated poly-carboxylic acids and cyclic anhydrides thereof are preferably ethylenically unsaturated dicarboxylic acids and cyclic anhydrides thereof and more preferably alpha, beta-ethylenically unsaturated dicarboxylic acids and cyclic anhydrides thereof.

Examples of such ethylenically unsaturated poly-carboxylic acids and cyclic anhydrides thereof include, but are not limited to, maleic acid, fumaric acid, maleic anhydride, itaconic acid, itaconic anhydride, citraconic acid, mesaconic acid, citraconic anhydride, aconitic acid (a tricarboxylic acid), aconitic anhydride, cis-4-cyclohexene-1,2-dicarboxylic acid, cis-4-cyclohexene-1,2-dicarboxylic anhydride, endo-cis-bicyclo (2,2,1)-5-heptene-2,3-dicarboxylic acid, and endo-cis-bicyclo (2,2,1)-5-heptene-2,3-dicarboxylic anhydride. These modifiers may be used alone or in combination thereof. Among these ethylenically unsaturated poly-carboxylic acids and cyclic anhydrides thereof, maleic acid, fumaric acid and maleic anhydride are particularly preferred, with maleic anhydride most preferred.

Examples of ethylenically unsaturated non-carboxylic monomers include, but are not limited to, vinyl ethers, vinyl esters, vinyl amides, olefins and diallyldialkyl ammonium halides.

Examples of vinyl ethers include, but are not limited to, vinyl methyl ether, vinyl dodecyl ether, divinyl ether, and vinyl isopropyl ether.

Examples of vinyl esters include, but are not limited to, vinyl acetate, vinyl stearate, and vinyl laurate.

Examples of vinyl amides include, but are not limited to, N-vinyl pyrrolidone.

Examples of olefins include, but are not limited to, ethylene, propylene, stryene, acrylonitrile, vinyl imidazole, vinyl pyridine and conjugated-dienes, for example, butadiene and isoprene.

Additionally, these copolymers may be block, tapered, random or regularly alternating copolymers. Again such copolymerization processes and methods and resulting polymers are well-known to those skilled in the art. An example of such block copolymers are HYPAN ® copolymers available from Kingston Technologies of Dayton, N.J., which include block copolymers of acrylic acid and acrylonitrile according to U.S. Pat. No. 4,420,589. An example of such regularly alternating polymers are UCARSET ® polymers available from Union Carbide Co., which include regularly alternating polymers of vinyl methyl ether and maleic anhydride.

In general, the amount of the active salt compound employed in the compositions of this invention will vary depending upon the particular pharmaceutical or therapeutic active being delivered, whether a diluent is present, the type of additives, and the like. In practice, however, it has been found that a concentration of the active salt compound in the composition can range up to about 30, preferably between about 0.05 and about 10 weight percent, based on the total weight of the composition of the delivery system.

The delivery systems of the present invention contain pharmaceutical and therapeutic actives that can be applied topically either singularly or in combination. Examples of these actives include, but are not limited to, compounds such as benzocaine (local anesthetic), amantadine (antiviral agent), miconazole (anti-fungal agent), Loceryl ® brand anti-fungal agent (available from Hoffman LaRoche, N.J.), naftifine (anti-fungal agent), minoxidil (vasodilator and anti-alopecia agent), nicotinate esters (vasodilator and anti-alopecia agent), diphenhydramine (anti-histamine), butorphanol (analgesic), propranolol (anti-arrhythmic), piroctone (kerolytic agent), erythromycin, and neomycin (antibiotics), and the like.

As indicated above, this list of pharmaceutical and therapeutic actives is not inclusive, but is presented merely to demonstrate the scope of the invention. A wide variety of other actives can be employed either alone or in combination. The only requirement is that these actives be capable of forming the active salt compound hereof.

The amount of active employed will be that amount necessary to deliver a pharmaceutically or therapeutically effective amount to achieve the desired result at the site of application. In particular, an effective amount depends, inter alia, upon the particular active, the severity of the condition, and other factors. In general, the concentration of the actives in the delivery systems can vary from as little as 0.01 up to 50 percent or higher, by weight of the delivery system. More typically, the active concentration is between about 0.01 and about 20 wt percent of the delivery system. Skilled practitioners will be able to adjust the quantity of active in the delivery system.

The delivery system of the present invention is particularly applicable to the delivery of actives which have limited solubility in biocompatible solvents and have a tendency to crystallize prior to absorption thereof into the applied area and then flake-off. In the active salt compound hereof, the active is ionically bound to the active salt compound on a molecular level. As such, crystallization of the active is prevented, or at least significantly inhibited, especially when applied to the application site.

Take for example a crystallizing active of interest such as minoxidil. The minoxidil is ionically bound to a carboxylic acid moiety of the polycarboxylic, biocompatible polymer, thereby forming the active salt compound.

Minoxidil has the following structure:

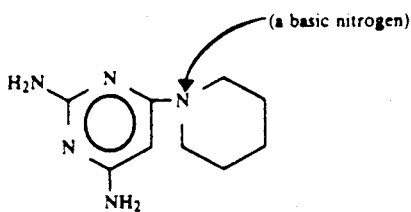

As noted above, minoxidil has a basic nitrogen. Thus, the structure thereof may be simplified for the purpose of illustration to that of a tertiary amine, i.e. $N-(R)_3$.

For illustrative purposes, the polycarboxylic acid, biocompatible polymer may be structurally simplified and represented as follows:

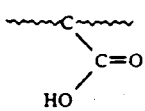

where the wavy line represents the backbone of the polymer.

The polycarboxylic acid, biocompatible polymer ionically complexes with the minoxidil in the following manner:

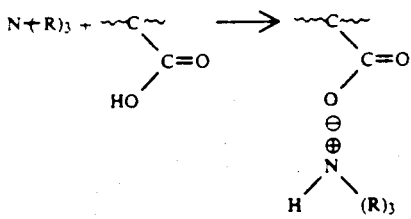

This active salt compound is a quaternary ammonium salt wherein the active is transformed into the quarternary ammonium moiety thereof (the cation) and the carboxylic acid moiety of the polymer is transformed into a negatively charged acid radical (the anion). Thus, as is readily apparent, the active, in this example minoxidil is ionically bound to the polymer on a molecular level.

Once the delivery system is applied to the subject, the active is released in an absorbable form and delivered to the application site. The exact nature of this release of the active from the active salt compound is not entirely understood. However, it is known that the active is released while the delivery system is in contact with the application site of the subject. Though not wishing to be bound to any particular theory, it is believed that moisture on the skin, for example, may cause the disassociation of the active therefrom, or that the acidity of the skin, for example, may cause an exchange of cations, i.e., a hydrogen from the acidic skin environment for the active in cation form. In any event, crystallization of the active has not been observed and the active is believed to be released in a molecular form and delivered in an absorbable form.

In addition to preventing, or at least inhibiting, crystallization of crystallizable actives, ionically bonding the active to the biocompatible polymer may also enhance the substantivity of the delivery systems, if the active imparts hydrophobic and/or amphoteric qualities to the polymer.

The delivery system of the present invention may optionally also contain a delivery enhancer. Typically, the delivery enhancer is a hydrophobic compound having limited solubility in water. These delivery enhancers enhance the delivery of actives which have limited solubility in water through a hydrophobic surface such as skin. A water-soluble active would migrate from a delivery system having an aqueous phase to the skin only with difficulty.

Examples of such delivery enhancers include, but are not limited to, benzyl alcohol, benzoate esters of $C_{12}-C_{18}$ alcohols, vaccenic acid (cis-octadecen-11-oic acid), hexylene glycol, AZONE, and dimethyl sulfoxide (DMSO).

If desired, the delivery systems of this invention can contain one or more pharmaceutically acceptable diluents or vehicles in addition to the active salt compound and the delivery enhancer. In many instances, the active salt compound itself can be about 0.5 to about 30 weight percent of the system with the remainder being diluent and optionally, other additives. Suitable diluents include water and among other, ethanol, isopropanol, glycerine, propylene glycol, hexylene glycol, polyethylene glycol, ethoxylated or propoxylated glucose, sorbitol derivatives, and the like, and aqueous mixtures thereof and combinations thereof.

Additives for the enhanced percutaneous absorption of various pharmaceutical or therapeutic actives also may be utilized. Such percutaneous enhancers include propylene glycol, glycerol, urea, diethyl sebecate, sodium lauryl sulfate, sodium laureth sulfate, sorbitan ethoxylates, nicotinate esters (such as hexyl nicotinate), oleic acid, pyrrolidone carboxylate ester, (such as dodecyl pyrrolidone carboxylate), N-methyl pyrrolidone, N,N-diethyl-m-toluamide, dimethyl sulfoxide, decyl methyl sulfoxide, alkyl methyl sulfoxides, N,N-dimethyl formamide, cis-11-octadecenoic acid, 1-dodecylazacycloheptan-2-one, and 1,3-dioxacyclopentane or 1,2-dioxacyclohexane containing at least one aliphatic group of four to eighteen carbon atoms.

Known methods for topically delivering certain actives typically require repeated applications during a 24-hour period to ensure that a sufficient quantity of active is delivered to the site. Repeated application is at best inconvenient, and at worst lead to uneven treatment, such as lack of treatment because the scheduled application time fell during a period of sleep, or at a time when application was impossible.

Repeated application of known topical treatments is necessary because the treatments cannot deliver a sufficient quantity of active in one application, e.g., without feeling greasy or delivering the active at an uneven rate. However, the delivery system of the invention affords an even delivery rate over a long period.

Delivery systems of the invention typically comprise lotions or oil-in-water emulsions. Oil-in-water emulsions feel relatively "non-greasy" when applied, whereas water-in-oil emulsions tend to have a greasy or oily feel. Therefore, oil-in-water emulsions are preferred by consumers.

Emulsion-type delivery systems of the invention are made by the "direct" method or by the "inversion" method. In the "direct" method, the oil phase is dispersed into the continuous aqueous phase to form the oil-in-water emulsion directly. An oil-in-water emulsion is made by the "inversion" method by emulsifying the aqueous phase into a continuous oil phase. At first, a water-in-oil emulsion is formed, but, as the quantity of aqueous phase is increased, the emulsion becomes "inverted" and forms an oil-in-water emulsion. Either preparation method can be used to prepare emulsion-type delivery systems of the invention.

The delivery enhancer also can act as an emulsifier between the oil phase and the aqueous phase. Addition of such an emulsifying delivery enhancer before the emulsion is formed typically causes the drop size of the oil phase to be smaller. Smaller drop size may contribute to increasing delivery efficiency.

The delivery enhancers of the invention are distinct from the above-described percutaneous enhancers. The percutaneous enhancers, typically act as humectants, lubricants, softening agents, moisturizers, debris removers, and impart cleansing and other effects. These enhancers therefore prepare the application site to receive active by ensuring that the site is softened, free of debris, and "amenable" to penetration.

In contrast, the delivery enhancers of the subject invention do not provide such functionalities. Rather, the delivery enhancers of the invention serve to provide a path or bridge through the skin, reduce the hydrophobicity of the skin, or otherwise delivering the active more efficiently by reducing the mutual repulsion of hydrophobic skin and hydrophobic actives (such as steroids).

The quantity of delivery enhancer should exceed the minimum quantity which will produce delivery enhancement. Addition of an excess quantity is not economically efficient. Therefore, the quantity of delivery enhancer is up to about 20 wt percent of the delivery system, preferably between about 0.25 and about 10 wt percent, and more preferably between about 0.5 and about 5 wt percent.

In practice, the delivery systems of the invention are readily formulated by mixing a non-aqueous fraction containing at least one delivery enhancer with a solution or suspension of the active salt compound. The solution or suspension of the active salt compound may be another non-aqueous fraction or an aqueous fraction depending upon the particular application and whether a suitable non-aqueous biocompatible solvent is available for the compound.

If the active salt compound is in an aqueous phase, an emulsion is formed if the non-aqueous fraction is not soluble in the aqueous phase together with a suitable emulsifier. Other adjuvant ingredients such as glycerine, propylene glycol, sorbitol, preservatives, stearic acid, cetyl alcohol, other high molecular weight alcohols, surfactants, menthol, eucalyptus oil, other essential oils, fragrances, penetration enhancers, and the like may be utilized to give stable delivery systems, such as a gel, cremes, ointments, lotions, and aerosols, may also be included.

Alternatively, solutions or mixtures of the active salt compound may be fabricated into films, rods, sheets, sponges, or fibers for use as suppositories, medicated sutures, medicated sheets, medicated bandages, patches, and the like.

The following examples are for illustrative purposes only and are not meant to limit the claimed invention in any manner.

Examples 1 to 3 are directed to different aspects of the delivery systems of the present invention. Examples 1 and 2 are directed to the synthesis of hydrophobe-modified carboxylic acid moiety-containing, biocompatible polymers, the acid moieties being in the cyclic anhydride form, and the formation of the active salt compound utilizing these polymers and minoxidil. Examples 2 and 3 demonstrate that high loadings of the active to the polymer are attainable. Example 3 further demonstrates the capability of the present delivery system regarding controlled or tailored active release rates.

For illustrative purposes only, the following examples utilize a copolymer of vinyl methyl ether and maleic anhydride. The specific polymer utilized is UCARSET polymer (DP-2500) available from Union Carbide Corporation. The UCARSET polymer (DP-2500) is a copolymer of an ethylenically unsaturated carboxylic acid or cyclic anhydride thereof and a vinyl ether, more specifically regularly alternating copolymer of vinyl methyl ether and maleic anhydride having a molecular weight of greater than about 25,000 and is in a solid, powdered form.

The family of UCARSET polymers are currently accepted and used as hair setting resins and denture adhesives. Thus, the delivery system of the present invention utilizing an active salt compound derived from a UCARSET polymer and minoxidil is an ideal media for hair growth treatments. As noted earlier, Examples 2 and 3 demonstrate that high loadings of minoxidil are attainable.

EXAMPLES

Throughout the Examples, all parts are parts by weight, unless otherwise identified.

EXAMPLE 1

Synthesis of Hydrophobe-modified UCARSET polymer (16242-75)

A 100 ml round bottomed flask was charged with 2.30 g of UCARSET polymer (DP-2500) and a solution of 0.58 g of dodecylamine in 46 g of absolute ethanol. The flask was fitted with a magnetic stirring bar and a Friedrich condenser with a drying tube. Heat was applied with a water bath, and the mixture was refluxed for six hours while stirring. The solid polymer gradually dissolved as it reacted, giving a clear, light yellow solution.

An infrared spectrum of this solution exhibited strong carbonyl bands at 1715 and 1650 cm$-1$, which are characteristic of ester and amide linkages, respectively. The absence of bands at 1780 or 1860 cm$-1$ indicated that all of the anhydride rings in UCARSET polymer had been reacted. A portion of the polymer was recovered by precipitation from diethyl ether. The dodecyl content of the solid polymer was measured by C13 NMR and was found to be 20.6 mole-%.

EXAMPLE 2

Dissolution of minoxidil in hydrophobe-modified UCARSET polymer (Preparation of active salt compound).

A 10% solution of hydrophobe-modified UCARSET polymer (16242-75) was prepared by dissolving 0.25 g of precipitated polymer 16242-75 in 2.36 g of 95% ethanol. To this solution was added 0.16 g of minoxidil, and the mixture was rolled on a roller mill for a few hours. The minoxidil had completely dissolved, giving a viscous, light yellow, homogeneous solution. The solution was stable and homogeneous after five weeks. The loading of minoxidil in this example was 0.64 g of minoxidil per gram of polymer.

EXAMPLE 3

Extraction of minoxidil in distilled water from active salt UCARSET polymer films Using the procedure described above, a 10% solution of hydrophobe-modified UCARSET polymer containing minoxidil (minoxidil loading of 0.40 g/g) was prepared (active salt compound). Films were cast from this solution. The films were clear and colorless, with no evidence of minoxidil crystallization or phase separation.

The extraction rate of minoxidil from these films was measured spectrophotometrically at 290 nm ($e = 12,045$ $M-1$ $cm-1$) in distilled water at 25° C. The apparent first order extraction rate and release half-life were measured using the method of K. Omata, et al., J. Appl. Polym. Sci., 21, 2009 (1977). The experiment was also repeated using the non-hydrophobe-modified half-ethyl ester of UCARSET polymer at the same minoxidil loading, and the results of these two experiments are given in the Table I below.

TABLE I

| Polymer Film | Extraction rate | Half-life of release |
| --- | --- | --- |
| Half-ethyl ester of UCARSET | 0.0877 hr$-1$ | 7.9 hr |
| Hydrophobe-modified UCARSET | 0.0534 hr$-1$ | 13 hr |

It is clearly evident that the presence of the hydrophobe decreases the rate of minoxidil extraction from the film. Thus, the delivery system of the present invention may be tailored to provide specific release rates by varying the hydrophobe content of the active salt compound.

I claim:

1. A biocompatible, film-forming delivery system for delivery of pharmaceutically or therapeutically effective amount of actives to a desired topical site of a subject, said system comprising:
   an active salt compound, wherein said active salt compound is at least a partial salt of
   (1) a carboxylic acid moiety-containing, biocompatible, film-forming polymer said carboxylic acid moiety-containing polymer being selected from the group consisting of polycarboxylic acid polymers and cyclic anhydride moiety containing polymers with
   (2) at least one active selected from the group consisting of pharmaceutical actives, therapeutic actives and a combination thereof, wherein said at least one active is capable of complexing with at least one carboxylic acid moiety of said polymer to form said active salt compound, and
   wherein said active salt compound forms an active salt compound film on said topical site and said active salt compound disassociates into said polymer and said at least one active while said delivery system is in contact with said topical site such that said polymer remains thereon as a polymer film and said at least one active is delivered to said topical site in an absorbable form.

2. The delivery system of claim 1 wherein said polymer is a homopolymer.

3. The delivery system of claim 1 wherein said polymer is a copolymer of an ethylenically unsaturated carboxylic acid or cyclic anhydride thereof and a vinyl ether.

4. The delivery system of claim 1 wherein said polymer is a graft polymer, said graft polymer having at least one carboxylic acid moiety grafted thereto.

5. The delivery system of claim 1 where said active has an amine moiety capable of complexing with at least one carboxylic acid moiety of said polymer to form said active salt compound.

6. The delivery system of claim 1 which is in the form of a film.

7. The delivery system of claim 1 which is in a form selected from the group consisting of a gel, a solution, a lotion, a cream and an ointment.

8. The delivery system of claim 1 which is in the form of a patch.

9. The delivery system of claim 1 which is in the form of an aerosol.

10. The delivery system of claim 1 which is in the form of a suppository.

11. The delivery system of claim 1 which is in the form of a fiber.

12. The delivery system of claim 1 which is in the form of a rod.

13. The delivery system of claim 1 which is in the form of microspheres.

14. A method for the preparation of a delivery system for use in administration of a pharmaceutically and, therapeutically effective amount of actives to a topical site of a subject, said method comprising:
   preparing an active salt compound by complexing
   (1) a carboxylic acid moiety-containing, biocompatible, film-forming polymer said carboxylic acid moiety-containing polymer being selected from the group consisting of polycarboxylic acid polymers and cyclic anhydride moiety containing polymers with
   (2) at least one active selected from the group consisting of pharmaceutical actives, therapeutic actives and a combination thereof and
   formulating said delivery system which comprises said active salt compound,
   wherein said at least one active is capable of complexing with at least one carboxylic acid moiety of said polymer to form said active salt compound, and
   wherein said active salt compound forms an active salt compound film on said topical site and said active salt compound disassociates into said polymer and said at least one active while said delivery system is in contact with said topical site such that said polymer remains thereon as a polymer film and said at least one active is delivered to said topical site in an absorbable form; which method comprises blending said active, said polymer, and a solvent and forming said active salt compound.

15. The method of claim 14 wherein said formulating step comprises blending a diluent with said active salt compound.

16. The method of claim 14 wherein said polymer is dissolved in a solvent before said complexing step.

17. The method of claim 14 wherein said active is dissolved in a solvent before blending.

18. A method for the topical administration of a pharmaceutical or therapeutic active to a subject, which comprises administering to said subject at a designated site, a pharmaceutically or therapeutically effective amount of the delivery system of claim 1.

19. The delivery system of claim 7 which is in the form of a solution.